United States Patent
Saeger et al.

(10) Patent No.: US 9,625,439 B2
(45) Date of Patent: Apr. 18, 2017

(54) METHOD FOR RECONCILING A MODEL OF COMPOSITION

(71) Applicants: Roland B Saeger, Runnemeade, NJ (US); Kaiyuan He, Bridgewater, NJ (US)

(72) Inventors: Roland B Saeger, Runnemeade, NJ (US); Kaiyuan He, Bridgewater, NJ (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 1012 days.

(21) Appl. No.: 13/832,747

(22) Filed: Mar. 15, 2013

(65) Prior Publication Data

US 2013/0325362 A1    Dec. 5, 2013

Related U.S. Application Data

(60) Provisional application No. 61/653,069, filed on May 30, 2012.

(51) Int. Cl.
  *G01N 33/28* (2006.01)
  *G06F 19/00* (2011.01)

(52) U.S. Cl.
  CPC ..... *G01N 33/2835* (2013.01); *G01N 33/2823* (2013.01); *G06F 19/704* (2013.01)

(58) Field of Classification Search
  CPC ............ G01N 33/2823; G01N 33/2835; G06F 19/704
  USPC ........................................ 702/22, 23, 27, 30
  See application file for complete search history.

(56) References Cited

U.S. PATENT DOCUMENTS

| | | | |
|---|---|---|---|
| 7,598,487 B2 | 10/2009 | Qian et al. | |
| 7,619,217 B2 | 11/2009 | Shea et al. | |
| 2009/0105966 A1* | 4/2009 | Brown | G01N 33/2823 702/30 |

OTHER PUBLICATIONS

Jaffe S.; FreundH.; Olmstead W.; Extension of Structure-Oriented Lumping to Vacuum Residua; 2005; American Chemical Society; Ind. Eng. Chem. Res. 2005, 44, 9840-9852.*

The International Search Report and Written Opinion of PCT/US2013/043284 dated Feb. 4, 2014.

Qian et al., "Determination of Structural Building Blocks in Heavy Petroleum Systems by Collision-Induced Dissociation Fourier Transform Ion Cyclotron Resonance Mass Spectrometry," Analytical Chemistry, 2012, vol. 84, No. 10, pp. 4544-4551.

(Continued)

*Primary Examiner* — Gregory J Toatley
*Assistant Examiner* — Terence Stifter, Jr.
(74) *Attorney, Agent, or Firm* — Andrew T. Ward; Glenn T. Barrett

(57) ABSTRACT

Method for determining the composition of a material, including obtaining a reference model of composition (MoC) of the material based on a molecular formula distribution of the material, and reconciling, using at least one computer processor, the reference MoC to match at least one target property of the material, is provided. The reference MoC can be expressed as a combination of molecular lumps with associated reference percent. The reconciliation can be carried out using by constrained optimization of information entropy, and the optimization can be performed on a more coarse-grained basis relative to the reference MoC.

12 Claims, 1 Drawing Sheet

(56) References Cited

OTHER PUBLICATIONS

Van Geem, et al., "Challenges of Modeling Steam Cracking of Heavy Feedstocks", Oil & Gas Science and Technology—Rev. IFP, vol. 63, pp. 79-94 (2008).
Hudebine, "Molecular Reconstruction of LCO Gasoils From Overall Petroleum Analyses", Chemical Engineering and Science, vol. 59, pp. 4755-4763 (2004).
Neurock, et al., "Molecular Representation of Complex Hydrocarbon Feedstocks Through Efficient Characterization and Stochastic Algorithms", Chemical Engineering and Science, vol. 49, pp. 4153-4177 (1994).
Jaffe et al., "Extension of Structure-Oriented Lumping to Vacuum Residua", Industrial & Engineering Chemistry Research, vol. 44, pp. 9840-9852 (2005).
McKenna, et al., "Heavy Petroleum Composition. 1. Exhaustive Compositional Analysis of Athabasca Bitumen HVGO Distallates by Fourier Transform Ion Cyclotron Mass Spectromethry: A Definitive Test of the Doduszynski Model," Energy & Fuels, vol. 24, pp. 2429-2938 (2010).

\* cited by examiner

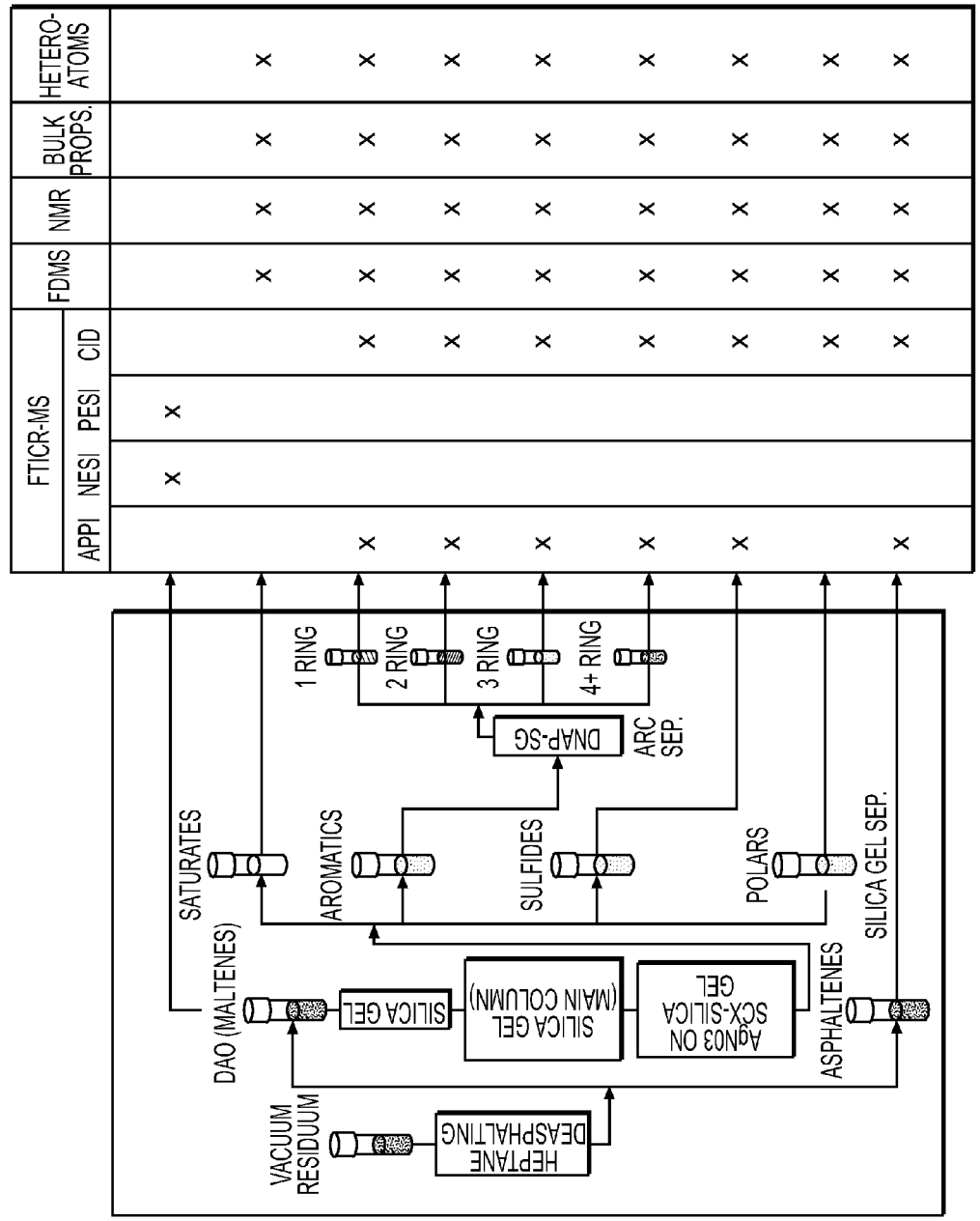

US 9,625,439 B2

METHOD FOR RECONCILING A MODEL OF COMPOSITION

BACKGROUND

Field of the Invention

The present application generally relates to methods for obtaining models of composition to compensate limitations of measurement techniques currently available.

Description of Related Art

Petroleum streams are complex mixtures of hydrocarbons containing enormous numbers of distinct molecular species. These streams include a variety of hydrocarbon streams from processes directed to the petroleum molecular composition. For example, virgin petroleum crude oils can contain molecules of a wide boiling point range from highly volatile C4 hydrocarbons to nonvolatile asphaltenes. The streams are extremely complex, and have numerous distinct molecular species. As such, any molecular approximation of the composition is essentially a model, that is, a model of composition (MoC). Analysis of petroleum composition of various boiling points is necessary for inputs to many subsequent processes.

Fourier Transform Ion Cyclotron Resonance (FTICR) mass spectrometry, together with a suitable ionization method, can be used can be used in constructing an initial estimate of the composition of a petroleum stream. Ionization methods used in conjunction with FTICR include Atmospheric Pressure Photoionization (APPI) and negative and positive ion electrospray (N-, PESI).

Despite FTICR's ultra-high mass resolution, this technique alone cannot provide sufficient information to construct an accurate model of composition beyond certain thresholds. For example, none of the identified ionization methods can efficiently ionize molecules in complex hydrocarbon mixtures that boil above 1250° F. Thus, known techniques cannot provide sufficient information to construct a Heavy Hydrocarbon Model of Composition (HHMoC) that is consistent with all features of the petroleum stream. HHMoC, as used herein, refers to a model of composition for a vacuum residuum (also known as resid) stream, i.e., petroleum streams that boil above 1000° F. In at least some resid streams, at least 50 weight percent of the molecules are known to boil above 1250° F. Thus, current ultrahigh resolution APPI-FTICR-MS (or N-, PESI-FTICR-MS) data does not lead to accurate estimates of molecular property distributions on the entire resid, or the entire resid fraction. Examples of FTICR-MS data based on the current technique are disclosed in available literature. See, e.g., McKenna, A. M., et al., "Heavy Petroleum Composition. 1. Exhaustive Compositional Analysis of Athabasca Bitumen HVGO Distillates by Fourier Transform Ion Cyclotron Mass Spectrometry: A Definitive Test of the Doduszynski Model," Energy & Fuels, v. 24, pp. 2429-2938, 2010.

Furthermore, APPI-FTICR-MS has poor ionization efficiency for molecules that boil above 1250° F. Relative to high-temperature Simdis measurements, FTICR severely under-predicts the amount of material boiling above 1250° F. Hence, it is not uncommon for FTICR to be unable to detect approximately 40 weight percent of the highest boiling material of a resid.

Complex hydrocarbon streams (e.g. crude petroleum, refinery intermediate and product streams) that boil below 1000° F. can be reconciled to High Detail Hydrocarbon Analysis (HDHA) or petroleum assays. Before the development of the HHMoC research analytical protocol, ExxonMobil researchers generated models-of-composition of resid streams. See e.g., Van Geem, K. M., et al., "Challenges of Modeling Steam Cracking of Heavy Feedstocks", Oil & Gas Science and Technology—Rev. IFP, v. 63, pp. 79-94, 2008; Jaffe, S. B., H. Freund, and W. N. Olmstead, "Extension of Structure-Oriented Lumping to Vacuum Residua", IEC Chem. Res., 44, pp. 9840-9852, 2005. Researchers at Institute Petrole de Francais (IFP, Lyon, France) and at the University of Ghent (Belgium) reconciled models-of-composition to HDHA-like analytical protocols. See Hudebine, D., J. J. Verstraete, "Molecular Reconstruction of LCO Gasoils from Overall Petroleum Analyses", Chem. Eng. Sci., v59, pp. 4755-4763, 2004. To date, there has not been public disclosure of models of composition reconciled to analytical protocols capable of analyzing petroleum streams with boiling points in the realm of HHMoC research analytical protocol (above 1000° F.).

Therefore, there is a need for a system and method to obtain model of composition that accurately describe the composition of resids at higher boiling points for HHMoC applications.

SUMMARY OF THE INVENTION

The purpose and advantages of the present application will be set forth in and apparent from the description that follows, as well as will be learned by practice of the disclosed subject matter. Additional advantages of the disclosed subject matter will be realized and attained by the method and system particularly pointed out in the written description and claims hereof, as well as from the appended drawings.

To achieve these and other advantages and in accordance with the purpose of the application, as embodied and broadly described, the disclosed subject matter includes a method for determining the composition of a material from a petroleum stream. The method includes obtaining a reference model of composition (MoC) for the material having a boiling point above about 1000° F. at atmospheric pressure, the reference MoC including a combination of molecular lumps having determined reference percent for each of the molecular lumps. The reference MoC is then reconciled using at least one computer processor to match at least one selected target property of the material to obtain a reconciled MoC representative of the composition of the material.

In some embodiments, the reconciled MoC includes updated percent for each of the molecular lumps. In some embodiments, the reconciling is performed under a constraint of the updated percent for each of the molecular lumps satisfying a set of property balance criteria regarding the at least one selected target property. In certain embodiments, each of the determined reference percent in the reference MoC is expressed as a function of the attributes of a Heavy Hydrocarbon Model of Composition (HHMoC) protocol.

In certain embodiments, the reference MoC of the material is based on a molecular formula distribution obtained the following method: obtaining an initial molecular formula distribution within a predetermined threshold for a sample of the material; identifying a correlation between two or more molecular properties of the initial molecular formula distribution; extrapolating, using at least one processor, the initial molecular formula distribution beyond the predetermined threshold along the correlation to construct an extrapolated molecular distribution; and renormalizing the extrapolated molecular formula distribution based on renormalization data obtained from the sample to generate a renormalized molecular formula distribution. The initial molecular formula distribution can include a fraction molecular formula distribution for each of a plurality of fractions, each of which can be a liquid chromatographic fraction selected from one of DAO saturates, DAO ARC1, DAO ARC2, DAO ARC3, DAO ARC4, DAO sulfides, DAO polars, asphaltenes, DAO aromatics, and DAO. The predetermined threshold is boiling point temperature of 1250° F. the renormalized molecular formula distribution include the determined reference percent of the molecular lumps in the reference MoC as defined by a HHMoC protocol. The method can further include blending the renormalized molecular formula distribution with the initial molecular formula distribution.

In some embodiments, reconciling the reference MoC is carried out by constrained optimization which comprises adjusting the reference percent of each of the molecular lumps to the updated percent. The at least one selected target property includes total weight of resid in the material, weight percentage of a fraction on total resid basis, or weight percentage of an element, such as hydrogen, sulfur, nitrogen, nickel, vanadium, of a fraction on total resid basis, the fraction being one of the fractions defined by a HHMoC protocol.

In exemplary embodiments, reconciling the reference MoC comprises adjusting the reference percent on a coarse-grained basis relative to the reference MoC. In particular embodiments, adjusting the reference percent comprises using a coarse-grained index related to a unique combination of attributes of fraction, hydrogen deficiency class, and molecular type as defined by a HHMoC protocol.

The at least one selected target property can be measurable by an analytic technique. For example, the analytic technique can be selected from one of super critical fluid chromatography, sulfur simulated distillation, simulated distillation, N and S elemental analysis, H-NMR and GC-Flame Ionization Detection.

BRIEF DESCRIPTION OF THE DRAWINGS

FIG. 1 is a schematic diagram of HHMoC Research Analytical Protocol.

DETAILED DESCRIPTION

While the disclosed subject matter may be embodied in many different forms, reference will now be made in detail to specific embodiments of the disclosed subject matter. This description is an exemplification of the principles of the disclosed subject and is not intended to limit the invention to the particular embodiments illustrated.

In accordance with one aspect of the disclosed subject matter, a method for determining the composition of a material is disclosed. The method includes obtaining a reference model of composition (MoC) for the material having a boiling point above about 1000° F. at atmospheric pressure, the reference MoC including a combination of molecular lumps having determined reference percent for each of the molecular lumps. The reference MoC is then reconciled using at least one computer processor to match at least one selected target property of the material to obtain a reconciled MoC representative of the composition of a material. In the reconciled MoC, the reference percent of the molecular lumps is updated such that the updated or reconciled percent of the molecular lumps can be more representative of the true MoC of the material.

In particular embodiments, the reference MoC of the material according to this method includes reference percent (hereinafter also referred to as "weights") for molecular lumps according to the Heavy Hydrocarbon Model of Composition (HHMoC) analytical protocol. For example, the reference MoC can be expressed as a combination of molecular lumps with associated reference percent, wherein each of the reference percent for the corresponding molecular lump is expressed as a function of the attributes defined by a HHMoC protocol, i.e., fraction index, molecular weight, hydrogen deficiency class, and molecular type, which is further described below.

Reference is now made to FIG. 1, which is a schematic diagram of the HHMoC analytical protocol. In this protocol, n-heptane separates a resid sample into de-asphalted oil (DAO), and asphaltene fractions. Next, a high-performance liquid-chromatographic (LC) technique separates the DAO into H-HDHA like fractions, e.g. saturates, ARC1-4, sulfides, and polars. These seven DAO fractions, and the asphaltene fraction, can be analyzed by a variety of methods. In each HHMoC fraction except DAO saturates and polars, ultra-high resolution Atmospheric-pressure Photoionization Fourier Transform Ion Cyclotron Resonance mass spectrometry (APPI-FTICR-MS) can be used to measure the molecular formula distribution. The molecule's molecular formula of resid can be given by $$C_c H_{2c+Z} S_s N_n O_o Ni_{ni} V_v \qquad (1)$$

Here, a molecule's carbon number is c, its hydrogen deficiency class Z, and s, n, o, are the stoichiometric coefficients of sulfur, nitrogen and oxygen, respectively. APPI-FTICR-MS has also detected organometallic compounds within selected resid fractions.

These organometallic (porphyrin) compounds contain one atom each of either nickel, or vanadium. In the molecular formula (1), the stoichiometric coefficients of nickel, and of vanadium, are ni, v, respectively.

In lieu of Eqn. (1), and as described herein, the molecular formulae of a molecule derived from FTICR-MS analysis can be expressed as a triplet of three attributes: the molecule's nominal mass, MW (g/mol), its hydrogen deficiency class, Z, and its molecular type, T. The molecular type T takes a naming convention that includes the number of heteroatoms (s,n,o), and metal atoms (ni, v) in a resid molecule (see Table 2). This reporting convention is equivalent to Eqn. (1); the carbon number c of a molecule can be uniquely determined because a molecule's nominal mass equals the sum of the nominal mass in each atom type within the said molecule, where the nominal mass in each atom type equals its known atomic mass (C=12, H=1, S=32, N=14, Ni=59, V=51) multiplied by the number of atoms of that type (c,2c+Z,s,n,ni,v). From this atomic mass balance, the carbon number, c reads:

$$c = (MW - (Z + 32s + 14n + 16o + 59ni + 51v))/14 \qquad (2)$$

Negative- and positive-ion electrospray (NESI- and PESI-) FTICR-MS can be performed on the DAO fraction to detect heteroatom-rich molecules that elute in a variety of LC fractions. NESI-FTICR-MS can detect non-basic nitrogen and acids; PESI-FTICR-MS detects primarily basic nitrogen compounds. The distribution of molecules comprising the DAO polar fraction can be assumed to be the superposition of the NESI- and PESI-FTICR-MS spectra.

Collision-induced dissociation (CID) can be used in conjunction with APPI-FTICR-MS to determine the molecular formulae of homologous series cores that comprise multi-core molecules that are abundant in selected HHMoC fractions that comprise resid (e.g. DAO ARC1-4, sulfides, polars, and asphaltenes).

At present, ultra-high resolution mass spectrometry techniques available in the HHMoC research analytical protocol cannot be applied to saturate molecules due to excessive fragmentation. Here, field desorption mass spectrometry (FDMS) can be used to estimate the nominal molecular weight distribution of each HHMoC DAO saturate fraction.

As described herein, molecular formula distribution of molecules are made consistent with the HHMoC analytical protocol. This distribution can be expressed mathematically as weight percent abundance (or simply "percent" or "weight") of molecular lumps (100 wt % resid basis), e.g., expressed as $w(f,MW,Z,T)$. The HHMoC fraction index takes positive integers, $f=1, 2, 3, \ldots 11$ and can be defined in Table 1.

TABLE 1

HHMoC Fraction Indices

| Fraction | Fraction Index, f |
|---|---|
| DAO Saturates | 1 |
| DAO ARC 1 | 2 |
| DAO ARC 2 | 3 |
| DAO ARC 3 | 4 |
| DAO ARC 4 | 5 |
| DAO Sulfides | 6 |
| DAO Polars | 7 |
| Asphaltenes | 8 |
| DAO Aromatics | 9 |
| DAO | 10 |
| Resid | 11 |

Molecular types, T, depend on the stoichiometric coefficients of heteroatoms, s, n, o and of metals ni, v. To date, a total of 35 molecular types can be used in HHMoC applications (see Table 2). All types except nickel porphyrins (T=4N1Ni, 1S4N1Ni) have been identified by ultrahigh resolution FTICR-MS. The nickel porphyrins can be "seeded" into the molecular formula distribution according to the co-pending U.S. Provisional Patent Application Ser. 61/653,061, filed on May 30, 2012, entitled "System and Method to Generate Molecular Formula Distributions Beyond a Predetermined Threshold for a Petroleum Stream," the disclosure of which is incorporated herein by reference in its entirety.

TABLE 2

Heteroatom Stoichiometric Coefficients of Molecular Types in HHMoC Applications

| Type, T | Stoichiometric coefficients | | | | |
|---|---|---|---|---|---|
| | s | n | o | ni | v |
| HC | 0 | 0 | 0 | 0 | 0 |
| 1S | 1 | 0 | 0 | 0 | 0 |
| 2S | 2 | 0 | 0 | 0 | 0 |
| 3S | 3 | 0 | 0 | 0 | 0 |
| 1N | 0 | 1 | 0 | 0 | 0 |
| 1S1N | 1 | 1 | 0 | 0 | 0 |
| 1O | 0 | 0 | 1 | 0 | 0 |
| 1N2O | 0 | 1 | 2 | 0 | 0 |
| 4N1O1V | 0 | 4 | 1 | 0 | 1 |
| 1S1O | 1 | 0 | 1 | 0 | 0 |
| 1S1N1O | 1 | 1 | 1 | 0 | 0 |
| 2S1O | 2 | 0 | 1 | 0 | 0 |
| 2S1N | 2 | 1 | 0 | 0 | 0 |
| 2S1N1O | 2 | 1 | 1 | 0 | 0 |
| 4S | 4 | 0 | 0 | 0 | 0 |
| 5S | 5 | 0 | 0 | 0 | 0 |
| 3N | 0 | 3 | 0 | 0 | 0 |
| 4N | 0 | 4 | 0 | 0 | 0 |
| 1S2N | 1 | 2 | 0 | 0 | 0 |
| 1S4N | 1 | 4 | 0 | 0 | 0 |
| 3S1O | 3 | 0 | 1 | 0 | 0 |
| 3S1N | 3 | 1 | 0 | 0 | 0 |
| 3S1N1O | 3 | 1 | 1 | 0 | 0 |
| 4S1N | 4 | 1 | 0 | 0 | 0 |
| 2O | 0 | 0 | 2 | 0 | 0 |
| 4O | 0 | 0 | 4 | 0 | 0 |
| 1N1O | 0 | 1 | 1 | 0 | 0 |
| 1S4N1O1V | 1 | 4 | 1 | 0 | 1 |
| 2N | 0 | 2 | 0 | 0 | 0 |
| 2N1O | 0 | 2 | 1 | 0 | 0 |
| 3N1O | 0 | 3 | 1 | 0 | 0 |
| 1S2N1O | 1 | 2 | 1 | 0 | 0 |
| 1S2O | 1 | 0 | 2 | 0 | 0 |
| 4N1Ni | 0 | 4 | 0 | 1 | 0 |
| 1S4N1Ni | 1 | 4 | 0 | 1 | 0 |

Nominal molecular weight, MW, can take any positive integer. However, nominal molecular weights appearing in FDMS spectra are truncated above 3000 g/mol. Hydrogen deficiency class, Z takes integers $Z=2, 1, 0, \ldots -\infty$. For molecules that have even numbers of nitrogen atoms, i.e. the stoichiometric index $n=0, 2, 4, \ldots$, the hydrogen deficiency class Z and the nominal molecular weight MW are even integers. For molecules with odd numbers of nitrogen atoms, i.e. $n=1, 3, 5, \ldots$, hydrogen deficiency class Z and molecular weight MW are odd integers.

In the HHMoC protocol, fraction weight percents can be normalized assuming 100% recovery in de-asphalting step, and in each of the DAO LC separation steps. Thus, the molecular formula distribution of the DAO aromatics fraction is sum of the distributions in the DAO ARC fractions:

$$w(9, MW, Z, T) = \sum_{f=2,3,4,5} w(f, MW, Z, T) \quad (3)$$

Likewise, the molecular formula distribution of the DAO fraction is the sum of the distributions in each of the silica-gel separation (SGS) fractions:

$$w(10, MW, Z, T) = \sum_{f=1,9,6,7} w(f, MW, Z, T) \quad (4)$$

Also, the molecular formula distribution of the total resid is the sum of the distributions in the DAO and asphaltene fractions:

$$w(11, MW, Z, T) = \sum_{f=8,10} w(f, MW, Z, T) \quad (5)$$

The term "obtain," as used herein, is meant to be broadly construed, and includes measuring the molecular formula distribution using one of the analytical techniques, generating the molecular formula distribution using a modeling technique, receiving a molecular formula distribution from a third party, and receiving information from a third party and thereafter generating a molecular formula distribution based in whole or in part on the received information.

The initial molecular formula can be obtained using an analytical technique. The analytical technique can be a multivariate analytical technique or any other analytical technique known in the art for its intended purpose. These techniques can include, for example, high-detail hydrocarbon analysis (HDHA), micro-hydrocarbon analysis (MHA), or ultrahigh resolution Fourier-transform Ion Cyclotron Resonance Mass Spectrometry (FTICR-MS). HDHA can be used to analyze complex hydrocarbon mixtures that boil below 1000° F. MHA is a similar analytical technique, but enables the analysis of selected hydrocarbon mixtures using smaller sample volumes than HDHA. MHA is more fully described in U.S. Pat. No. 7,598,487, which is incorporated herein by reference in its entirety.

Ultrahigh resolution FTICR-MS can be used in conjunction with a number of ionization methods. These ionization methods can include, for example, Atmospheric Pressure Photoionization (APPI), Negative and Positive-Ion Electrospray Ionization (NESI or PESI), Matrix-Assisted Laser Dissociation Ionization (MALDI), and Desorption Electrospray Ionization (DESI), and Laser Induced Acoustic Desorption (LIAD). LIAD is described in greater detail in U.S. Pat. No. 7,619,217.

In accordance with one aspect of the disclosed subject matter, the disclosed subject matter includes a method to extrapolate molecular formula distributions beyond a predetermined threshold is provided. The method generally includes obtaining an initial molecular formula distribution within a predetermined threshold for a sample of a material from the petroleum stream; identifying a correlation between two or more molecular properties of the initial molecular formula distribution; extrapolating, using at least one processor, the initial molecular formula distribution beyond the predetermined threshold to construct an extrapolated molecular distribution; and renormalizing the extrapolated molecular formula distribution based on renormalization data obtained from the sample to generate a renormalized molecular formula distribution. In a further aspect, the renormalized molecular formula distribution can be blended with the initial molecular formula distribution to maintain a similar level of detail contained in the initial molecular formula distribution at boiling points below the predetermined threshold (e.g., boiling point threshold). These aspects of the disclosed subject matter and various embodiments thereof are more fully described in the co-pending U.S. Provisional Patent Application Ser. 61/653,061, filed on May 30, 2012, entitled "System and Method to Generate Molecular Formula Distributions Beyond a Pre-determined Threshold for a Petroleum Stream," as noted above. As embodied herein, this method is generally described with reference to extrapolating a molecular formula distribution beyond a predetermined boiling point threshold, e.g., at 1250° F. However, one of skill in the art will appreciate that other molecular properties can be used as the predetermined threshold. The predetermined threshold can also be, for example, a molecular weight threshold. The fraction can be of any suitable size, number, and characteristic. Furthermore, the disclosed subject matter also encompasses the extrapolation of a molecular formula distribution for the sample of the petroleum stream as a whole. As such, the molecular properties used in constructing the correlation can include the boiling point of the entire petroleum stream and the boiling point of one or more fractions (e.g., each liquid chromatographic fraction).

In the above method, the initial molecular formula distribution can be obtained using an analytical technique, for example, high-detail hydrocarbon analysis, micro-hydrocarbon analysis, ultrahigh resolution Fourier Transform Ion Cyclotron Resonance mass spectrometry, and/or the procedure outlined in the HHMoC applications described above in reference to FIG. 1. The analytical technique can also be a multivariate analytical technique. Alternatively, and in accordance with another embodiment, the initial molecular formula distribution can be obtained using a modeling technique. The modeling technique can be, for example, composition-based process modeling, which creates the molecular formula distribution as the molecular formula distribution of a product or intermediate stream whose composition is computed within a process model. The modeling technique can also be composition synthesis modeling, wherein the molecular formula distribution is derived from analytical techniques, but has been adjusted to match its own bulk properties, or that of another hydrocarbon stream. The modeling technique can also be theory-based modeling, wherein the distribution of molecules, and hence molecular formulae, is predicted by a theory that can be reduced to a computer-based algorithm. An example of a theory-based modeling technique is the Anderson-Schulz-Flory distribution arising in Fischer-Tropsch synthesis. A more complex example is petroleum, whose molecular distributions can be approximated by combining geochemical-based rules of formation, e.g., isoprene alkylation, biodegration, thermo-chemical sulfate reduction.

Additional aspects of obtaining a MoC for a material can be understood generally from co-pending U.S. Provisional Patent Application Ser. 61/653,061, filed on May 30, 2012, entitled "System and Method to Generate Molecular Formula Distributions Beyond a Predetermined Threshold for a Petroleum Stream," the disclosure of which is incorporated herein by reference in its entirety.

After obtaining the MoC of a sample of material, for example, according to the above-described extrapolation procedure (which optionally includes blending the renormalized molecular formula distribution with the initial molecular formula distribution), the molecular formula distribution can be reconciled to match selected target property or properties of the material to obtain a reconciled model of composition representative of the composition of the material. The target property or properties can be measurable by an analytical technique, including, but not limited to, super critical fluid chromatography, sulfur simulated distillation, simulated distillation, N and S elemental analysis, H-NMR and GC-Flame Ionization Detection. The reconciliation procedure generally includes tuning or adjusting the reference percent of the molecular lumps to obtain updated percent such that the selected target property or properties are matched by the reconciled molecular weight distribution having the updated percent or weights. For example, a vector of autotuned (or reconciled) molecular lump percent or weights $\{w_i\}$ can be determined that minimizes the loss of information entropy upon adjustment from the reference percent or weight $\{w^*_i\}$ (which can be obtained as the output of the extrapolation procedure as described above), subject to the constraint that the updated percent or weights $\{w_i\}$ satisfy a linear system of property balance equations regarding the selected target property or properties:

$$\sum_{i=1}^{N} a_{ji} w_i = b_j \text{ for } j = 1, 2, \ldots, NP \qquad (6)$$

where $a_{ji}$ is the density of property j in molecular lump i, and $b_j$ is the measured value of property j. For purpose of illustration and not limitation, some exemplary target properties are provided in Table 3 below.

TABLE 3

Selected Target Property (or Property Balance Constraints) in Reconciliation

| Target Property, b | Index of HHMoC fractions, f | Non-zero values of property density, a | Softness parameter, η |
|---|---|---|---|
| Total weight (100 wt % resid basis) | All fractions, i.e. f = 1, 2, 3, . . . , 11 | a = 1 for all molecules | 0 |
| Fraction wt %, total resid basis | All fractions except DAO saturates, i.e. f = 2, 3, 4, . . . , 11 | a = 1 for all molecules in fraction f | 0 |
| Hydrogen wt % in fraction, total resid basis | All fractions, i.e. f = 1, 2, 3, . . . , 11 | a = weight fraction hydrogen for all molecules in fraction f | 1.0E−06 |
| Sulfur wt % in fraction, total resid basis | All fractions except DAO saturates, i.e. f = 2, 3, 4, . . . , 11 | a = weight fraction sulfur for all molecules in fraction f | 1.0E−06 |
| Nitrogen wt % in fraction, total resid basis | f = 6, 7, 8, 9 only | a = weight fraction nitrogen for all molecules in fraction f | 1.0E−06 |
| Nickel wt % in fraction, total resid basis | f = 8, 10 if data available; f = 11 otherwise | a = weight fraction nitrogen for all molecules in fraction f | 0 |
| Vanadium wt % in fraction, total resid basis | f = 8, 10 if data available; f = 11 otherwise | a = weight fraction vanadium for all molecules in fraction f | 0 |

In one embodiment, the weights in the above Eqn. (6) can be determined by constrained optimization of information entropy, e.g., by solving the following Euler-Lagrange equation to determine a set of Lagrange multipliers $\lambda_k$:

$$\sum_{i=1}^{N} a_{ji} w_i * \exp\left(-1 + \sum_{k=1}^{NP} \lambda_k a_{ki}\right) = b_j \exp(-\eta_j \lambda_j) \text{ for } j = 1, \ldots, NP \quad (7)$$

In Equation (7), the number of Lagrange multipliers equals the number of linear property constraints, NP (of order 10-100) which is often much smaller than N, the number of molecular lumps (1000-10,000 in typical HDHA applications). The softness parameters $\eta_j$ are zero to denote hard constraints. Otherwise, they are non-zero to facilitate convergence of the Euler-Lagrange Eqn. (7) when selected measured properties $b_j$ have significant uncertainty; non-zero values of these parameters can be determined by trial and error. Some of exemplary parameter values can be chosen from Table 3 above.

The above Eqn. (7) can be solved on a computer for the Lagrangian multipliers $\{\lambda_k\}$, e.g., using Newton's method. Then, the vector of autotuned or updated lump percent or weights $\{w_i\}$ can be determined by the following Eqn. (8):

$$w_i = w_i * \exp\left(-1 + \sum_{j=1}^{NP} a_{ij} \lambda_j\right) \text{ for } i = 1, \ldots, N \quad (8)$$

The number of molecular lumps in the reference MoC, e.g., expressed as molecular formula distribution w*(f,MW,Z,T), can be large in the sample material being analyzed, e.g., N≈100-300,000 for resids. Additional aspects of the methodology and procedure used for reconciling a model of composition can be understood from U.S. Patent Publication No. 2009/0105966, which is incorporated herein by reference in its entirety.

The reconciliation method described above can be carried out by adjusting the lump percent or weights on a more coarse-grained basis. For example and not limitation, the coarse-graining procedure can group molecular lumps with similar molecular properties, e.g., having one or more attributes (f, MW, Z, T) in common, into a single lump such that the total number of molecules/lumps to be used in the reconciling algorithm is significantly reduced. In this manner, the coarse-graining not only can improve computational efficiency for solving the above linear equations, but also can make the mathematical solutions of computed physical properties more closely correspond their expectant values based on physical principles. For example and not limitation, to maintain smoothness in the autotuned or reconciled molecular formula distribution w(f,MW,Z,T), the coarse-graining method can use a transformation defined by:

$$w(f,MW,Z,T) = w^*(f,MW,Z,T)\Psi(f,Z,T) \quad (9)$$

where the initial value of the coarse-grained weights $\Psi^*(f, Z,T)=1$. The coarse-graining method defined in Eqn. (9) ensures that the shape of the autotuned molecular formula distribution w(f,MW,Z,T) with respect to nominal molecular weight MW is the same as that of the input molecular formula distribution w*(f,MW,Z,T). Upon substitution of Eqn. (9) into the Euler-Lagrange Eqn. (7), the following Eqn. (10) is obtained:

$$\sum_{m=1}^{M} A_{jm} \exp\left(-1 + \sum_{k=1}^{NP} \lambda_k A_{km}\right) = b_j \exp(-\eta_j \lambda_j) \text{ for } j = 1, \ldots, NP \quad (10)$$

where $$A_{jm} = \sum_{MW} a_{ji} w^*(f, MW, Z, T) \quad (11)$$

Here, the molecular lump index i identifies a unique combination of attributes {f,MW,Z,T}, and the coarse-grained index m identifies a unique combination of the attributes {f,Z,T}. In this manner, the variable MW is collapsed in the coarse-graining and is not directly used in solving Eqn. (7). As such, the complexity of solving Eqn. (7) can be greatly reduced.

It is noted that the other alternative coarse-graining procedure can be used. For example, other attributes or variables of freedom can be chosen. For example, one or more of the attributes f, Z, or T in the molecular formula distribution function w(f,MW,Z,T) can be chosen to be collapsed. However, the resulting transformed equations from Eqn. (7) may be not as rigorous or efficient to solve compared with the above Eqns. (10) and (11) where the attribute of MW is collapsed.

Again, the above algebraic Eqn. (10) can be solved on a computer for the Lagrangian multipliers $\{\lambda_k\}$, e.g., using Newton's method. Once these Lagrangian multipliers have been solved, the autotuned molecular formula distribution w(f,MW,Z,T) can be computed from the Lagrange multipliers according to the following Eqn. (12) that combines Eqns. (9-11):

$$w(f, MW, Z, T) = w*(f, MW, Z, T)\exp\left(-1 + \sum_j A_{jm}\lambda_j\right) \quad (12)$$

While the present application is described herein in terms of certain preferred embodiments, those skilled in the art will recognize that various modifications and improvements can be made to the application without departing from the scope thereof. Thus, it is intended that the present application include modifications and improvements that are within the scope of the appended claims and their improvements. Moreover, although individual features of one embodiment of the application may be discussed herein and not in other embodiments, it should be apparent that individual features of one embodiment can be combined with one or more features of another embodiment or features from a plurality of embodiments.

In addition to the specific embodiments claimed below, the application is also directed to other embodiments having any other possible combination of the dependent features claimed below and those claimed above. As such, the particular features presented in the dependent claims and disclosed above can be combined with each other in other manners within the scope of the application such that the application should be recognized as also specifically directed to other embodiments having any other possible combinations. Thus, the foregoing description of specific embodiments of the application has been presented for purposes of illustration and description. It is not intended to be exhaustive or to limit the application to those embodiments disclosed.

The invention claimed is:

1. A method for determining the composition of a material from a petroleum stream, comprising:
   obtaining a reference model of composition (MoC) for the material having a boiling point above about 1000° F. at atmospheric pressure, the reference MoC including a combination of molecular lumps having determined reference percent for each of the molecular lumps; wherein obtaining the reference MoC includes;
   separating a sample of the material into one or more fractions;
   obtaining an initial molecular formula distribution within a predetermined threshold from the one or more fractions of the sample of the material; wherein the predetermined threshold is a boiling point temperature of 1250° F.;
   identifying a correlation between two or more molecular properties of the initial molecular formula distribution;
   extrapolating, using at least one processor, the initial molecular formula distribution beyond the predetermined threshold along the correlation to construct an extrapolated molecular distribution; and
   renormalizing the extrapolated molecular formula distribution based on renormalization data obtained from the sample to generate a renormalized molecular formula distribution;
   measuring at least one selected target property of the material;
   wherein the at least one target property includes at least one of total weight of the resid in the material, weight percentage of a fraction on total resid basis, weight percentage of hydrogen of a fraction on a total resid basis, weight percentage of sulfur of a fraction on a total resid basis, weight percentage of nitrogen of a fraction on a total resid basis, weight percentage of nickel of a fraction on a total resid basis, weight percentage of vanadium of a fraction on a total resid basis, the fraction being one of the fractions defined by a Heavy Hydrocarbon Model of Composition (HH-MoC) protocol; and
   reconciling, using at least one computer processor, the reference MoC to match the at least one selected target property of the material to obtain a reconciled MoC representative of the composition of the material.

2. The method of claim 1, wherein the reconciled MoC includes updated percent for each of the molecular lumps.

3. The method of claim 1, wherein the reconciling is performed under a constraint of the updated percent for each of the molecular lumps satisfying a set of property balance criteria regarding the at least one selected target property.

4. The method of claim 1, wherein each of the determined reference percent in the reference MoC is expressed as a function of the attributes of a Heavy Hydrocarbon Model of Composition (HHMoC) protocol.

5. The method of claim 1, wherein the method for obtaining the molecular formula distribution further comprises blending the renormalized molecular formula distribution with the initial molecular formula distribution.

6. The method of claim 1, wherein the initial molecular formula distribution comprises a fraction molecular formula distribution for each of a plurality of fractions.

7. The method of claim 1, wherein each of the plurality of fractions is a liquid chromatographic fraction selected from one of de-asphalted oil ("DAO") DAO saturates, DAO aromatic ring class ("ARC") ARC1, DAO ARC2, DAO ARC3, DAO ARC4, DAO sulfides, DAO polars, asphaltenes, DAO aromatics, and DAO.

8. The method of claim 1, wherein the renormalized molecular formula distribution include the determined reference percent of the molecular lumps in the reference MoC as defined by a HHMoC protocol.

9. The method of claim 1, wherein reconciling the reference MoC is carried out by constrained optimization which comprises adjusting the reference percent of each of the molecular lumps to the updated percent.

10. The method of claim 9, wherein adjusting the reference percent to the updated percent comprises adjusting the reference percent on a coarse-grained basis relative to the reference MoC.

11. The method of claim 10, wherein adjusting the reference percent comprises using a coarse-grained index related to a unique combination of attributes of fraction, hydrogen deficiency class, and molecular type as defined by a HHMoC protocol.

12. The method of claim 1, wherein the analytic technique is the measuring at least one selected target property of the material is accomplished by selected from one of super critical fluid chromatography, sulfur simulated distillation, simulated distillation, N and S elemental analysis, H-NMR and GC-Flame Ionization Detection.

* * * * *